(12) United States Patent
Van Rijn et al.

(10) Patent No.: US 8,936,160 B2
(45) Date of Patent: Jan. 20, 2015

(54) NOZZLE DEVICE AND NOZZLE FOR ATOMISATION AND/OR FILTRATION AND METHODS FOR USING THE SAME

(75) Inventors: Cornelis Johannes Maria Van Rijn, Hengelo (NL); Jeroen Mathijn Wissink, Enschede (NL); Wietze Nijdam, Apeldoom (NL)

(73) Assignee: Aquamarijn Holding B.V., Hengelo (NL)

( * ) Notice: Subject to any disclaimer, the term of this patent is extended or adjusted under 35 U.S.C. 154(b) by 0 days.

(21) Appl. No.: 13/448,048

(22) Filed: Apr. 16, 2012

(65) Prior Publication Data

US 2012/0228238 A1 Sep. 13, 2012

Related U.S. Application Data

(62) Division of application No. 12/073,387, filed on Mar. 5, 2008, now abandoned, which is a division of application No. 11/101,391, filed on Apr. 8, 2005, now Pat. No. 7,963,466, which is a division of application No. 10/362,761, filed as application No. PCT/NL01/00630 on Aug. 28, 2001, now abandoned.

(30) Foreign Application Priority Data

Aug. 28, 2000 (NL) ..................... 1016030

(51) Int. Cl.
*B01D 37/00* (2006.01)
*B01D 39/00* (2006.01)
(52) U.S. Cl.
USPC ............ 210/483; 210/767; 239/596; 347/93; 347/47

(58) Field of Classification Search
None
See application file for complete search history.

(56) References Cited

U.S. PATENT DOCUMENTS

| | | | |
|---|---|---|---|
| 3,586,907 A | 6/1971 | Beam et al. |
| 4,601,777 A | 7/1986 | Hawkins et al. |
| 4,628,576 A | 12/1986 | Giachino et al. |
| 4,768,751 A | 9/1988 | Giachino et al. |
| 4,789,425 A | 12/1988 | Drake et al. |
| 4,828,184 A | 5/1989 | Gardner et al. |
| 4,864,329 A | 9/1989 | Kneezel et al. |
| 4,871,489 A | 10/1989 | Ketcham |
| 4,875,968 A | 10/1989 | O'Neill et al. |
| 5,002,230 A | 3/1991 | Norskav et al. |
| 5,124,717 A | 6/1992 | Campanelli et al. |
| 5,201,987 A | 4/1993 | Hawkins et al. |
| 5,204,690 A | 4/1993 | Lorenze et al. |
| 5,320,290 A | 6/1994 | Rohs et al. |
| 5,543,046 A | 8/1996 | Van Rijn |

(Continued)

FOREIGN PATENT DOCUMENTS

| | | |
|---|---|---|
| EP | 879635 | 11/1998 |
| WO | 9323154 | 11/1993 |

(Continued)

*Primary Examiner* — Robert James Popovics
(74) *Attorney, Agent, or Firm* — Joseph F. Aceto, Esq.

(57) ABSTRACT

Nozzle device and nozzle for atomisation and/or filtration as well as methods for using the same. The present invention relates to a nozzle and nozzle device for atomisation, in particular a micro-machined reinforced nozzle plate, that may produce small liquid droplets in air (spray) or into a liquid (emulsion) with a narrow droplet size distribution and to make small air bubbles into a liquid (foam) and to methods of making the same. The invention is further related to a nozzle part for filtration as well as means and methods to facilitate atomisation and filtration.

13 Claims, 21 Drawing Sheets

(56) References Cited

U.S. PATENT DOCUMENTS

| | | |
|---|---|---|
| 5,651,900 A | 7/1997 | Keller et al. |
| 5,753,014 A | 5/1998 | Van Rijn |
| 5,925,205 A | 7/1999 | Zimmermann et al. |
| 6,016,969 A | 1/2000 | Tilton et al. |
| 6,036,105 A | 3/2000 | Sanada et al. |
| 6,036,832 A | 3/2000 | Knol et al. |
| 6,044,981 A | 4/2000 | Chu et al. |
| 6,084,618 A | 7/2000 | Baker |
| 6,086,195 A | 7/2000 | Bohorquez et al. |
| 6,113,976 A | 9/2000 | Chiou et al. |
| 6,130,688 A | 10/2000 | Agarwal et al. |
| 6,189,214 B1 | 2/2001 | Skeath et al. |
| 6,189,813 B1 | 2/2001 | Skeath et al. |
| 6,207,369 B1 | 3/2001 | Wohlstadter et al. |
| 6,352,209 B1 | 3/2002 | Skeath et al. |
| 6,378,788 B1 | 4/2002 | Skeath et al. |
| 6,464,347 B2 | 10/2002 | Kneezel et al. |
| 6,513,736 B1 | 2/2003 | Skeath et al. |
| 6,652,077 B2 | 11/2003 | Maeng et al. |
| 6,679,101 B1 | 1/2004 | Rohner |
| 6,756,019 B1 | 6/2004 | Dubrow et al. |
| 6,769,765 B2 | 8/2004 | Kneezel et al. |
| 6,780,340 B2 | 8/2004 | Conta |
| 6,797,945 B2 | 9/2004 | Berggren et al. |
| 6,849,459 B2 | 2/2005 | Gilbert et al. |
| 6,878,271 B2 | 4/2005 | Gilbert et al. |
| 7,094,345 B2 | 8/2006 | Gilbert et al. |
| 7,531,120 B2 | 5/2009 | Van Rijn et al. |
| 7,963,466 B2 * | 6/2011 | Van Rijn et al. ............... 239/596 |
| 2001/0019029 A1 | 9/2001 | Tai et al. |
| 2003/0150791 A1 | 8/2003 | Cho et al. |
| 2003/0178507 A1 | 9/2003 | Maria Rijn Van |
| 2004/0028875 A1 | 2/2004 | Van Rijn et al. |
| 2005/0115889 A1 | 6/2005 | Schaevitz et al. |
| 2005/0178862 A1 | 8/2005 | Van Rijn |
| 2007/0227591 A1 | 10/2007 | Wissink et al. |
| 2008/0217262 A1 | 9/2008 | Van Rijn |
| 2008/0248182 A1 | 10/2008 | Jongsma et al. |
| 2012/0228238 A1 * | 9/2012 | Van Rijn et al. ............... 210/767 |

FOREIGN PATENT DOCUMENTS

| | | |
|---|---|---|
| WO | 9513860 | 5/1995 |
| WO | 9740213 | 10/1997 |
| WO | 9801228 | 1/1998 |
| WO | 9801705 | 1/1998 |
| WO | 2005105276 | 11/2005 |

* cited by examiner

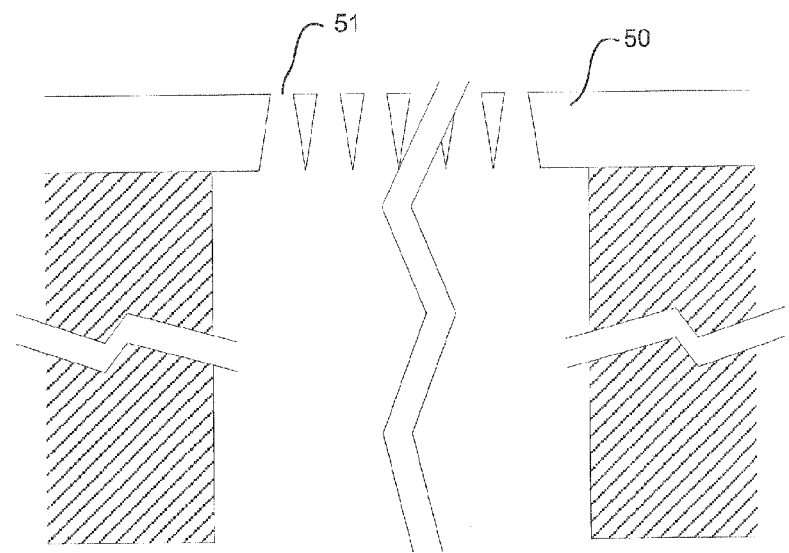
Fig. 8A
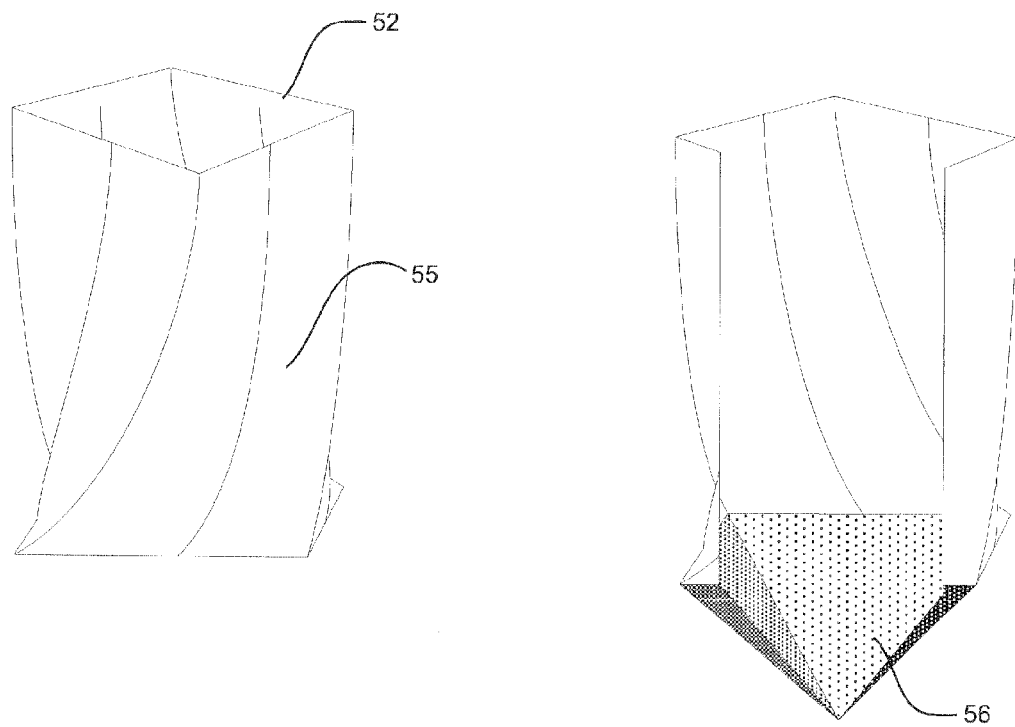
Fig. 8B
Fig. 8C

NOZZLE DEVICE AND NOZZLE FOR ATOMISATION AND/OR FILTRATION AND METHODS FOR USING THE SAME

This application is a division of co-pending application Ser. No. 12/073,387, filed on Mar. 5, 2008, which is a division of co-pending application Ser. No. 11/101,391, filed on Apr. 8, 2005. Application Ser. No. 11/101,391 is a division of Ser. No. 10/362,762, filed on Feb. 26, 2003, which is is the national phase of PCT International Application No. PCT/NL01/00630 filed on Aug. 28, 2001 under 35 U.S.C. §371, which claims priority of Netherlands Application No. 1016030 filed Aug. 28, 2000. The entire contents of each of the above-identified applications are hereby incorporated by reference.

The present invention relates to a nozzle device having a nozzle for atomisation of a fluid, the nozzle comprising a nozzle plate support body having a cavity extending from a first main surface to a second main surface thereof, and comprising a nozzle plate having at least one nozzle orifice in fluid communication with said cavity at said first main surface side of said nozzle plate support body. The invention further relates to a nozzles as used in such a nozzle device.

These devices are used for filtration purposes and or for atomisation of a fluid to produce small liquid droplets in air (spray) or into a liquid (emulsion) with a relatively narrow droplet size distribution and to make small air bubbles into a liquid (foam) and to methods of using the same. The device and especially the nozzle plate may be produced by micro-machining (Micro System Technology) which means that the subject nozzle part means are produced using lithography steps related to semiconductor fabrication methods. Alternatively spark erosion and laser drilling techniques may be used, but in general these tend to be less reproducible and less precise in comparison with micro-machining methods.

The performance of many atomisation devices can be improved if the atomising device provides very small droplets with a very narrow pore size distribution.

For example, small droplets between 2 and 3 micron in diameter improve the effectiveness of medical atomisers because of the high (80%) deposition intake deep into the lungs. Also the stability of an emulsion (o/w, w/o) is greatly improved if the emulsion droplets are all of equal size. Besides that, the structural and rheological properties of many foams in the dairy industry can be improved by the use of very small air bubbles with a narrow size distribution.

The disadvantage of many conventional atomising devices is that they break bulk liquid or gas into relatively large droplets through use of stirring or turbulence. By more input of energy the large droplets will be broken up in smaller droplets. As the droplets become smaller than 20-100 microns, they become harder to break and secondary atomisation typically ceases. The droplet size distribution is in most cases rather broad.

It is known from fuel injectors that nozzle structures may be used for obtaining a very fine spray for combustion improvement. Such small nozzle structures however are very sensitive for fouling and unwanted leakage due to blocked nozzle orifices. For a high throughput of equally sized droplets normally an array of identical nozzles is used. However if one or more nozzle orifices becomes blocked the size distribution will broaden. If a nozzle orifice becomes smaller through partial blockage the droplets of this orifice will also become smaller. Moreover if the blockage is very severe spraying(or jetting) will cease and liquid will flow through this orifice over the surface of the nozzle structure hence influencing or inhibiting spraying behaviour of the other orifices.

It is also known that very small nozzles suffer from a threshold pressure (Pascal pressure/capillary forces) before they start spraying. The threshold pressure is inversely proportional to the nozzle diameter. For a nozzle with a diameter of 1 micron this pressure is typical 1-3 bar. For an array of nozzles it is therefore very important that all nozzles have an equal geometry with narrow tolerances and that the threshold pressure is kept as low as possible.

A high flow rate can be achieved by choosing the flow resistance of each nozzle orifice as small as possible and/or by increasing the pressure difference over the orifice during jetting. Practically the jetting pressures are chosen to be fairly higher than typical 5-10 bar. Such pressures will exert high forces on the nozzle plate. The nozzle plate is therefore chosen fairly thick (>4-5 micron) in order to withstand such forces. However a thick nozzle plate implies a long orifice length and thus a high flow resistance and subsequently a reduced flow rate.

SUMMARY OF THE INVENTION

It is inter alia an object of the invention to provide a nozzle device and a nozzle of the type referred to in the opeing paragraph in which these drawbacks have been counteracted at least to an impressive exntend.

To this end a nozzle device as described in the opening paragraph is according to the invention characterized in that said support body is provided with filtration means which comprise a filtration plate which is in fluid communication with said cavity at said second main surface side of said nozzle plate support body.

A further object of the present invention is to produce a properly constructed nozzle plate for atomisation at operational pressures smaller than 10 bar.

Another object of the present invention is to provide nozzle plates that produce droplets typically with a mean diameter of 10 micron or smaller with a very narrow droplet distribution.

Yet another object of the present invention is to provide nozzle plates for small handheld atomising devices with a throughput nearly independent of the viscosity of the fluid (e.g. medicine) and means to reproducible facilitate atomisation.

Yet another object of the present invention is to produce a properly constructed nozzle plate (filtration membrane) for filtration of small and large amounts of liquid or gas and means to facilitate filtration with such a filtration membrane, which may be used in combination with atomisation applications.

Yet another object of the invention is to provide nozzle plates for large atomising devices capable of substantial throughput of atomised liquid or gas.

Yet another object of the invention is to provide nozzle plates with orifices with a reduced flow resistance that can withstand high operational pressures.

Yet another object of the invention is to provide atomising devices that are rather insensitive for microbiological fouling and unwanted leakage due to blocked nozzle orifices.

Yet another object of the invention is to provide atomising devices that are less sensitive for the Pascal threshold pressure.

These and additional objects and advantages of the invention will become apparent from the technical description which follows.

BRIEF DESCRIPTION OF THE DRAWINGS

FIG. 8A is a cross section of a thick nozzle plate with reduced flow resistance.

FIG. 8B is a cross section of a spiral nozzle orifice.

FIG. 8C is a cross section of the manufacturing method of a spiral nozzle orifice.

FIG. 19 is a cross section high performance filter with the possibility for light to pass through.

TECHNICAL DESCRIPTION OF THE PREFERRED EMBODIMENTS

Figure 1:
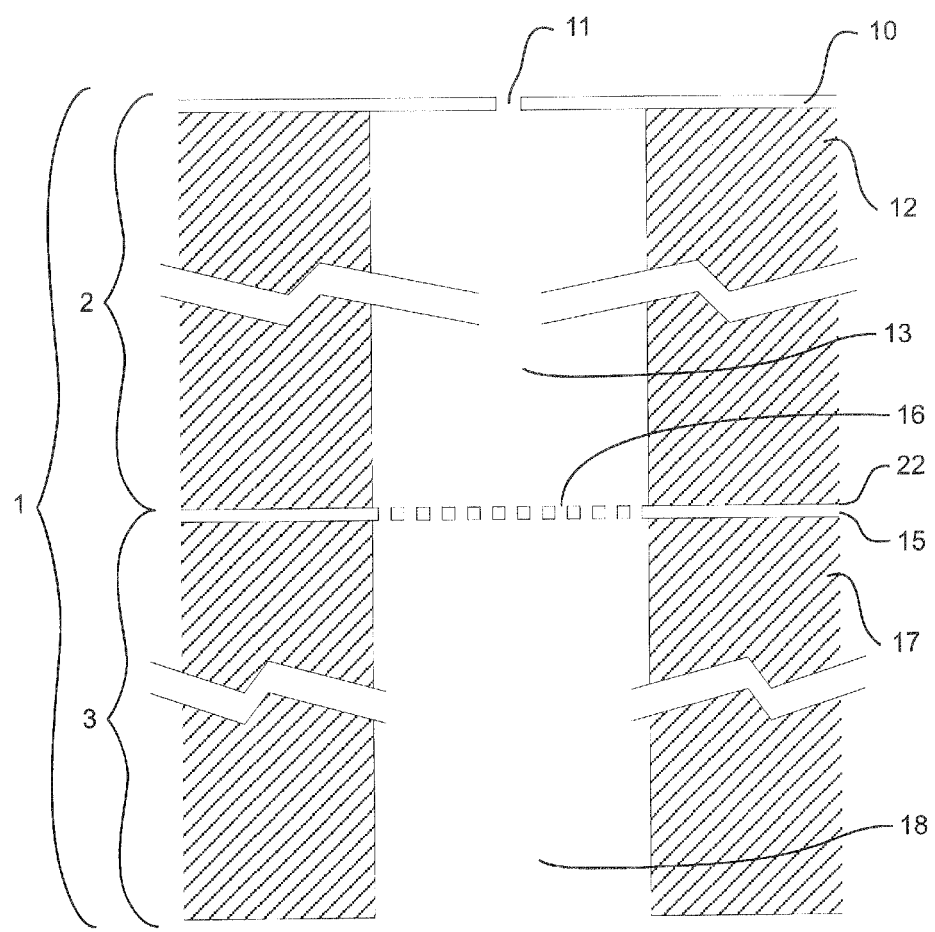
FIG. 1 is a cross section of a nozzle device with a nozzle plate and pre-filter for atomisation.

A first embodiment of a nozzle device 1 is shown in FIG. 1. The nozzle device 1 comprises a nozzle for atomisation 2, with a nozzle plate 10 with at least one nozzle orifice 11 and a nozzle plate support body 12 with a nozzle cavity 13, further comprising filtration means 3 with a filtration plate 15 with at least one filtration orifice 16 and a filtration plate support body 17 with at least one filtration cavity 18. This nozzle device 1 is rather insensitive for microbiological fouling and unwanted leakage due to blocked nozzle orifices 11 because of the placement of a pre-filter for the nozzle for atomisation 2. Basically the nozzle for atomisation 1 and filtration means 2 are made with the same micro machining techniques giving many additional advantages. The two parts 2 and 3 may have similar size and flatness and can therefor easily be directly bonded or glued 22 together without the need of separate or elaborated connection parts, that may introduce particle contamination between the nozzle plate 11 for atomisation and filtration plate 15. A silicon wafer containing a number of nozzles for atomisation and a silicon wafer with a number of filtration means may be first bonded together before sawing the wafer sandwich into separate dies with individual nozzle and filtration means.

Figure 2:
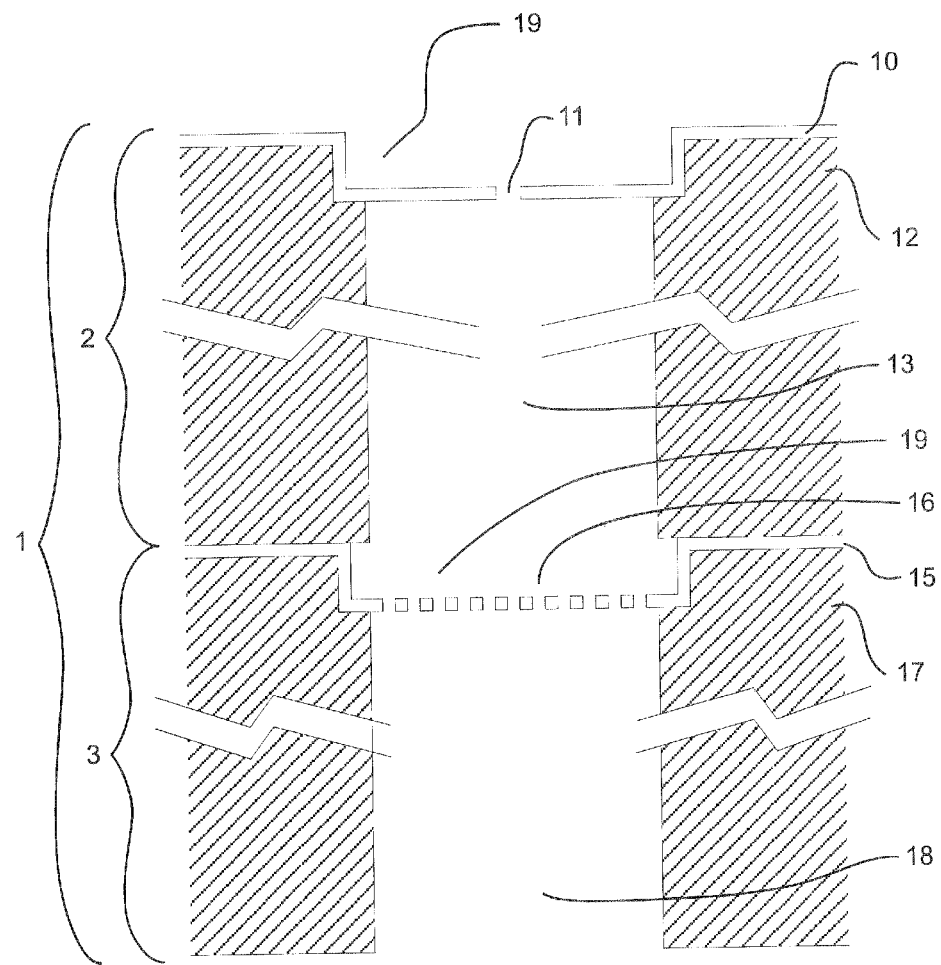
FIG. 2 is a cross section of a nozzle device with a nozzle plate and pre-filter for atomisation, in which the nozzle plate and the pre filter are deepened for protection.
Figure 3:
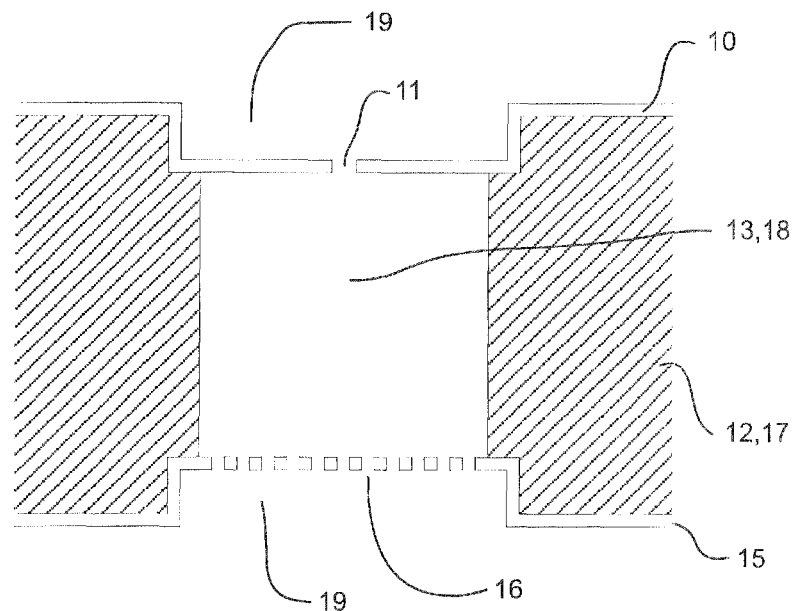
FIG. 3 is a cross section of a nozzle device with a nozzle plate and pre-filter for atomisation made from one piece.
Figure 4:
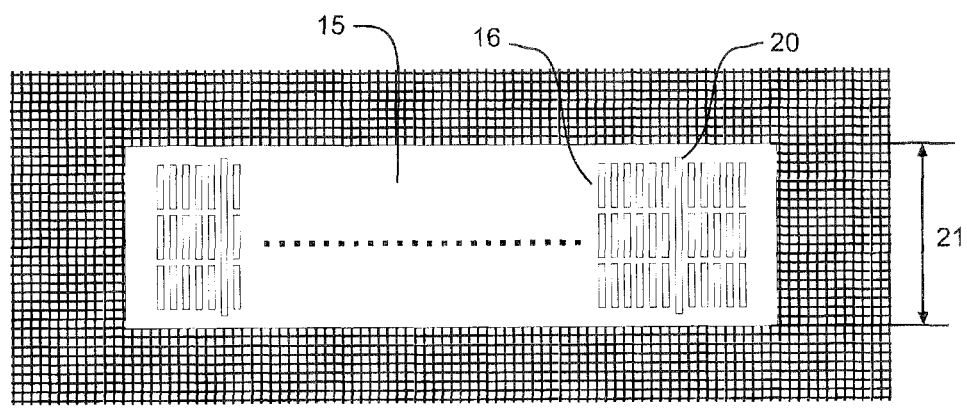
FIG. 4 is a top view of a nozzle plate containing slits plus special slits for pressure reduction.
Figure 5A:
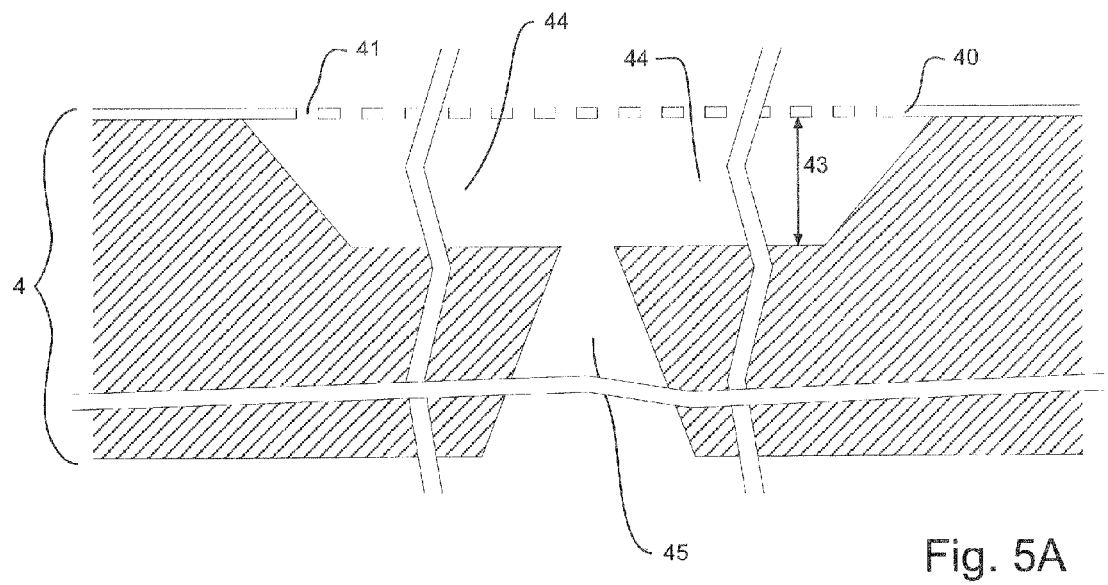
FIG. 5A is a cross section of a nozzle device containing more orifices to increase the throughput.
Figure 5B:
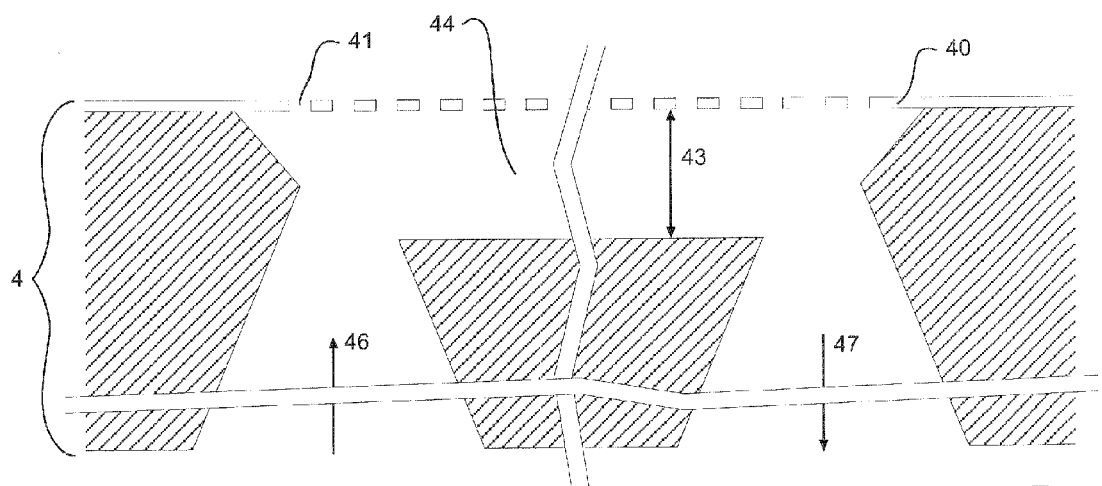
FIG. 5B is a cross section of a nozzle device containing more orifices to increase the throughput with the possibility of liquid flow on both sides of the membrane.
Figure 6:
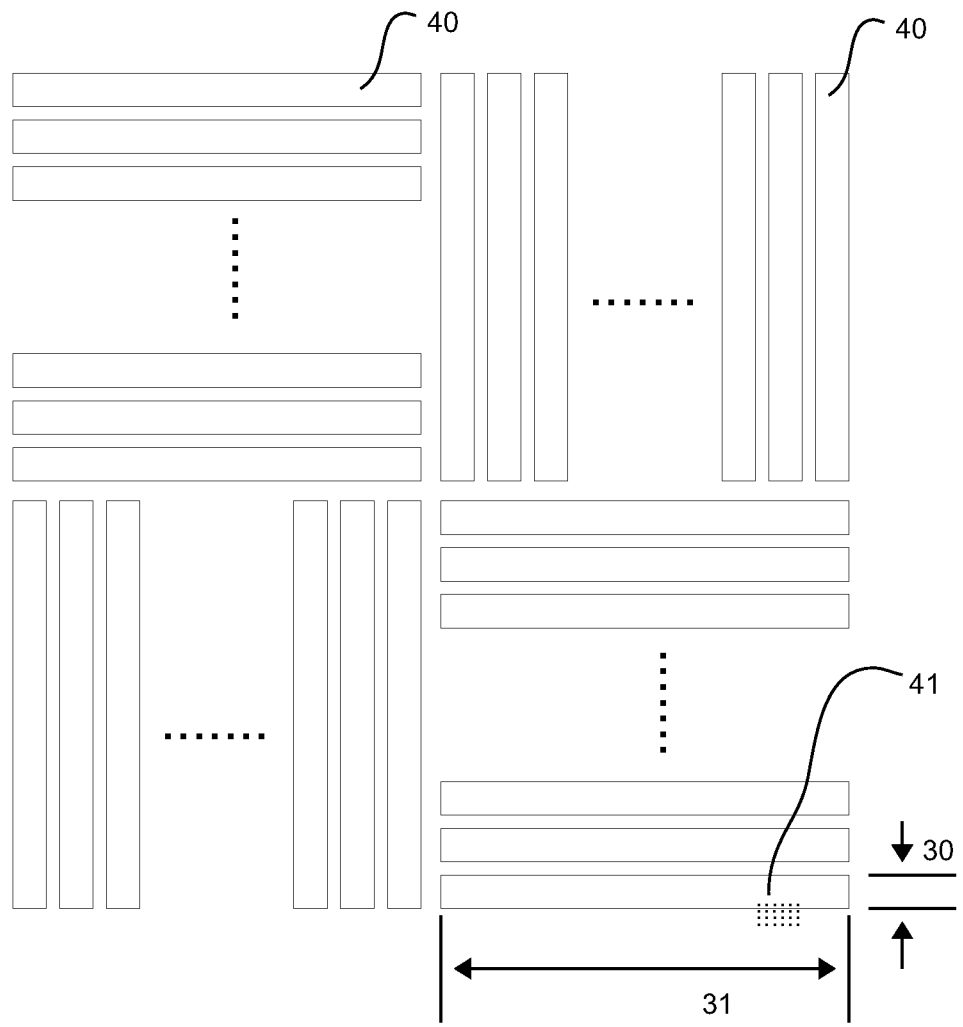
FIG. 6 is a top view of closely packed nozzle plates.
Figure 7A:
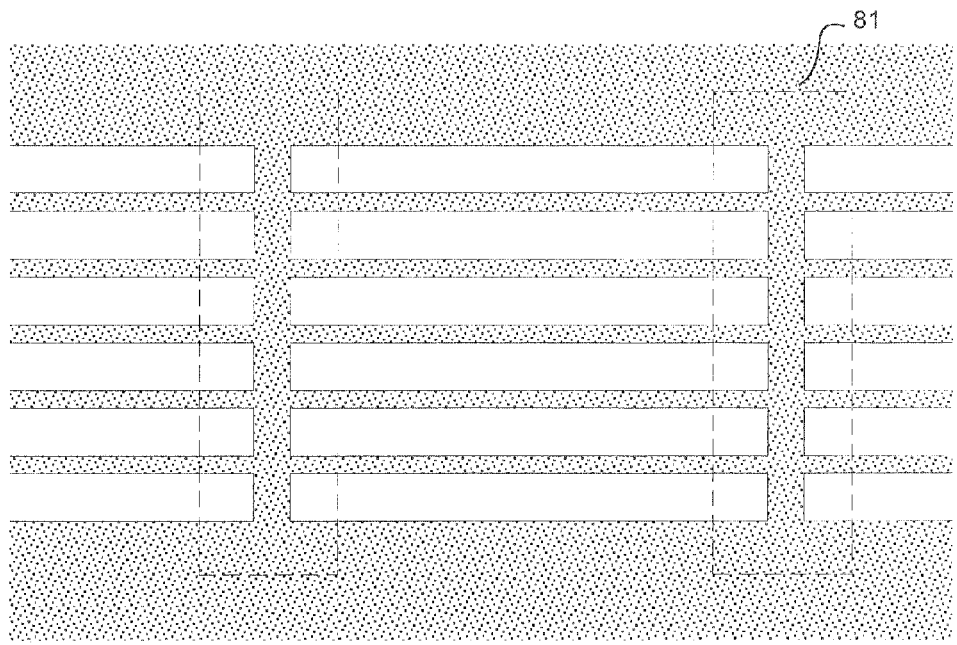
FIG. 7A is a top view of interconnected nozzle plates.
Figure 7B:
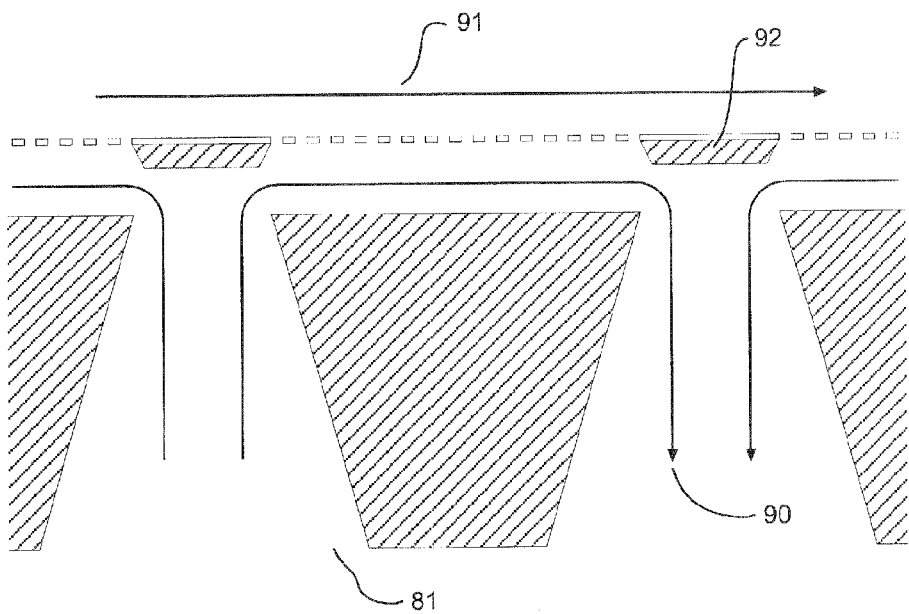
FIG. 7B is a cross section of interconnected nozzle plates.

Another embodiment of a nozzle device 1 is shown in FIG. 2, characterised in that the nozzle orifices 11, 16 are made in a 2-200 micron deepened region 19 of the nozzle plate 2,3 with respect to the nozzle plate support body 12 and filtration plate support body 17, herewith protecting the nozzle and/or filtration means during manufacturing and assembly against scratches etc. With preference the nozzle plate support body 12 and filtration plate support body 17 are identical, FIG. 3, the cavities 13,18 are then made by etching the support material directly through the nozzle and filtration orifices 11,16. With this manufacturing process there can not be any particle contamination between the filtration plate 15 and the nozzle plate for atomisation 10. In some cases it has been proven useful to make in the filtration means 3 one or more filtration orifices substantially larger (1-3 micron) than the other ones (0.2-0.8 micron) in order to reduce the Pascal pressure or to facilitate the removal of etching material(gas). Alternatively the filtration orifices 16 are slit-shaped to reduce the Pascal pressure. A special embodiment of such a filtration plate has a number of very long slit shaped filtration orifices 20 (e.g. with a length of 50-100 micron) near the edges of the filtration plate. Depending on the width 21 of the filtration plate 15 (e.g. 100 micron) and the applied pressure (e.g. 1 bar) this slit will open due to local bending of the filtration plate 15 (FIG. 4). Preferably the fluid resistance of the filtration plate 15 is minimal 3 times smaller than the fluid resistance of the nozzle plate 10. By this the pressure across the nozzle device 1 is effectively only used for atomisation.

Nozzles for atomisation 2 can be made with known micro machining techniques. A mono crystalline silicon wafer 12 with thickness 400 micron is provided with a Low Pressure Chemical Vapour Deposition grown layer 10 of low stress silicon nitride with a thickness of 1 micron. With a suitable mask a photo lacquer pattern with 2 micron orifices at the front side of the wafer 12 and a similar pattern with 15 micron openings at the back side is being exposed and developed. With the aid of anisotropic reactive ion etching a nozzle orifice 11 with a diameter of 2 micron and a length of 1 micron is made in the silicon nitride layer and with use of dry and wet chemical KOH etching a cavity 13 with a diameter of 15 micron and a length of 400 micron is made in the silicon wafer 12.

The flow rate Φ of a medium or a liquid with viscosity η through an orifice (tube) with length L and diameter D for viscous flow at a pressure difference ΔP is given by the law of Poiseuille: $\Phi_{Poiseuille}=\pi D^4\Delta P/128L\eta$. A parabolic velocity pattern with a low velocity along the wall and a high velocity in the middle of the tube will settle in case the length of the tube L is larger than typical six times the diameter D. The mean velocity v of the medium or liquid is always given by $v=4\Phi/\pi D^2$.

In case the length L is of the order of the diameter D the law of Poiseuille will change to the law of Stokes: $\Phi_{stokes}=D^3\Delta P/24\eta$. The parabolic velocity pattern will not be valid in this regime. Dagan et al., Chem. Eng. Svi., 38 (1983) 583-596 have proposed an interpolation formula for both regimes: $\Phi_{Dagan}=D^3\Delta P/24\eta\ [1+16L/3\pi D]^{-1}$.

At large velocities v the viscous regime will not be valid any more because another force/pressure is necessary for a kinetic (inertial) contribution to accelerate the medium or fluid to a velocity v. This pressure difference is given by $\Delta P_{kin}=0.5\rho v^2$, with ρ the mass density of the fluid v (cf. Law of Bernoulli).

An important insight according to the invention is that the total needed pressure $\Delta P_{tot}$ is the sum of the viscous and the kinetic contribution:

$$P_{tot}=\Delta P_{vis}+\Delta P_{kin}=6\eta\pi[D+16L/3\pi]^{-1}\ v+0.5\ \rho\ v^2.$$

Typical for a waterbased fluid and for a thin orifice this means:

$$\Delta P_{tot}\approx 18.000D^{-1}\ v+500\ v^2$$

(L<D, $n=10^{-3}$ poise, $\rho=1000$ kg/m$^3$, D in micron, v in m/s, ΔP in Pascal). At a $\Delta P_{kin}$ of 4 bar ($=4\times10^5$ Pascal) the maximum jet velocity will be 28 m/s. $\Delta P_{vis}$ will be for this velocity 500.000 $D^{-1}$. In case D>2 micron than $\Delta P_{vis}<2.5$ bar. $\Delta P_{tot}$ is then 4+2.5=6.5 bar, less than the maximum of 10 bar. However in case L/D>2 then at D=2 micron the needed pressure will surely exceed 10 bar.

Another important insight is that with a very thin orifice (L≈D≈micron) both in the viscous and in the kinetic regime all the fluid will leave the orifice as a jet with constant velocity v (no parabolic velocity distribution). Especially the kinetic energy of the jet will make that the jet will prolong its track before it breaks up in small droplets, which is particularly useful for Rayleigh break-up of the jet in droplets in air. Rayleigh droplets have a typical droplet size 1.6 times the diameter D of the out coming jet. The fabrication tolerance in the diameter D of the nozzle orifice is an essential factor in determining the amount of liquid ($\Delta V=4\pi(1.6D/2)^3/3$) in a Rayleigh droplet. The United States FDA imposes a repeatability of 20% for 90% of the droplets and 25% for the remaining 10%. Only micro machining methods are capable of producing orifices with a tolerance less than 3% (=variation in ΔV<10%). Also because micro machining is done in a sterile and particle free Clean Room environment also the effect of fouling of the nozzles due to particles and/or micro organisms is avoided.

Another important insight according to the invention is that for a very thin orifice(L≈D≈micron) the flow rate at relatively low pressures (3-10 bar) is mainly determined by the kinetic contribution, which means that viscosity of the fluid (medicine) has a minor role as long as L≈D and $\eta<10^{-2}$ poise. Jetting (e.g. Rayleigh break-up) with a nozzle plate with a thickness less than 2 micron and orifices with a diameter between 0.4 and 10 micron at a pressure in which the contribution of the kinetic regime ($0.5\rho v^2$.) is larger than the contribution of the viscous regime ($6\eta\pi[D+16L/3\pi]^{-1}.v$) is therefore a very good method to deliver and dose medicines nearly independent of the viscosity of the medicine.

Another important insight according to the invention is that medicine (e.g. proteins and peptides) degradation is strongly diminished if such thin orifices are used at relatively low jetting pressures (<10 bar) with a minimum of shear in strength, time and length of the medicine in passing such an orifice.

Using the law of Stokes and Poiseuille (or Dagan) it is easily to calculate that the flow resistance of the 2 micron orifice 11 is still 5-10 times higher than the flow resistance of the cavity 13 with diameter 15 micron and length 400 micron. This means that the pressure/flow characteristics of this structure is still mainly determined by the 2 micron orifice.

In preference the thickness of the nozzle plate 10 for atomisation is less than six times the diameter of the nozzle orifice 11 and in preference less than one to two times the diameter in order to prevent the built up of a parabolic velocity distribution. The flow resistance may be further reduced through the manufacturing of tapering orifices although it is well known that the amount of tapering is very difficult to control precisely. In case the nozzle plate 10 has a thickness less than 2 micron it still has sufficient strength and it is not necessary to taper the orifices.

Nozzles can be used for as well atomisation and filtration. An embodiment of a nozzle with a nozzle orifice for atomisation or filtration 4 is shown in FIG. 5A, 5B and topview FIG. 6. The nozzle plate 40 comprises more nozzle orifices 41 placed next to each other in order to increase the throughput. The nozzle plate 40 with a thickness of 1 micron of low stress silicon nitride has a width of less than 250 micron 30 and a length of more than 300 micron 31. The maximum pressure strength of each nozzle plate 40 is well above 10 bar. A nozzle plate 40 with a width of 100 micron has a pressure strength well above 20 bar. A number of those nozzle plates 40 are closely packed with a mean distance less than 100 micron offering a large effective nozzle plate area as seen in topview FIG. 6.

The nozzle 4 comprises further at least one shallow flow channel 44 connected to the nozzle plate 40 with a mean depth of minimum 10 and of maximum 300 micron connected to the nozzle plate. This depth 43 is dependent on the size and number of the nozzle orifices 41 in the nozzle plate 40. The flow resistance of the flow channel 44 in the nozzle plate support should be at least one to ten times smaller than the flow resistance of the nozzle plate 40 itself. In case the total flow resistance of the nozzle plate support as defined by regions 44 and 45 is one to five times the flow resistance of the nozzle plate 40 a nice flow limitation has been constructed in case the nozzle plate 40 would disrupt. Alternatively two or more openings 46,47 can be provided in each nozzle plate to promote fluid flow and the removal of particles and air bubbles underneath the nozzle plate 40.

Cross-flow cleaning 90,91 on both sides of the nozzle plate is enhanced by the interconnection 81 in one or more directions of all nozzle plate support flow channels 44 (FIG. 7A,7B). Silicon bars 92 between the nozzle plates 40 may be provided for enhanced strength.

Subsequently the nozzle plate 50 may be chosen thicker than a few micron with corresponding tapering orifices 51 in order to reduce the flow resistance still further, shown in FIG. 8A. A good measure is also to make spiral grooves 55 in the nozzle orifice 51 to give the medium a rotational motion when leaving the orifice 51, shown in FIG. 8B. Anisotropic and directional etching techniques with $SF_6$ and $O_2$ at low bias-voltage 10-40 eV make it possible to make such grooves in e.g. a <100> silicon wafer. The groove 55 will start at a defined rectangular orifice 52, the groove will turn and will stop turning as defined by the orientation of the <111> planes 56 shown in FIG. 8C.

Figure 9:
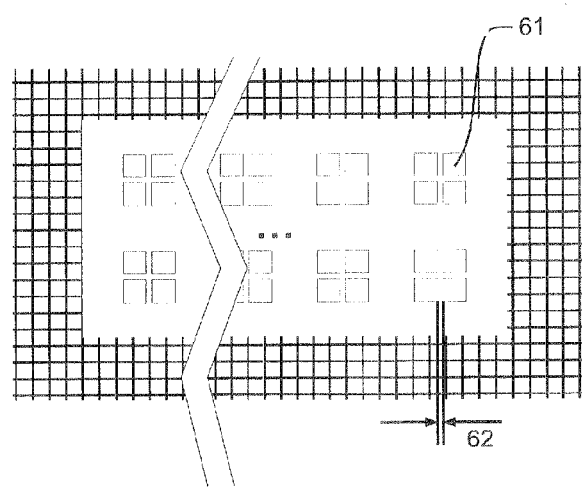
FIG. 9 is a top view of nozzle plate with improved jetting behaviour.

With preference a number of nozzle orifices 61 are placed very close together (FIG. 9), which improves flow rate, filtration and kinetic jetting behaviour, e.g. 2 or more nozzle orifices with a diameter of 2 micron may be separated with a mean distance less than 0.5 micron 62.

Figure 10A:
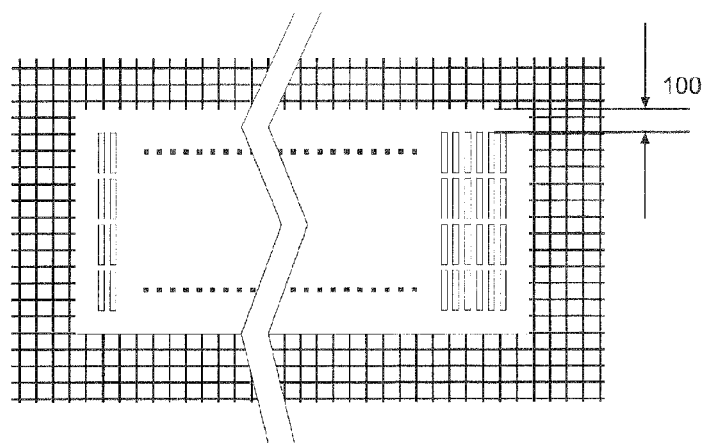
FIG. 10A is a top view of a substantially stronger nozzle plate with slit type orifices.
Figure 10B:
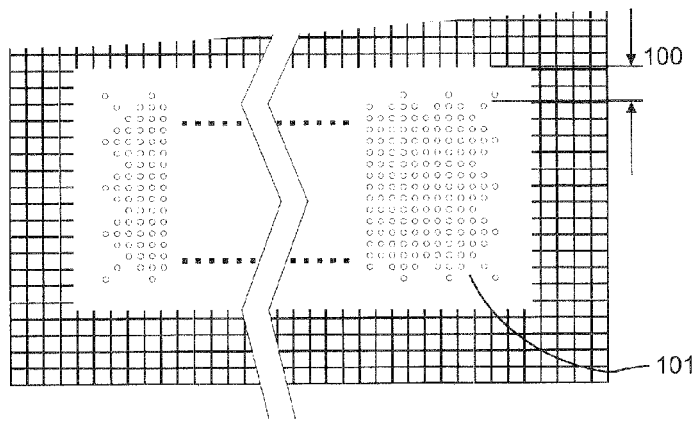
FIG. 10B is a top view of a substantially stronger nozzle plate with circular orifices.
Figure 11:
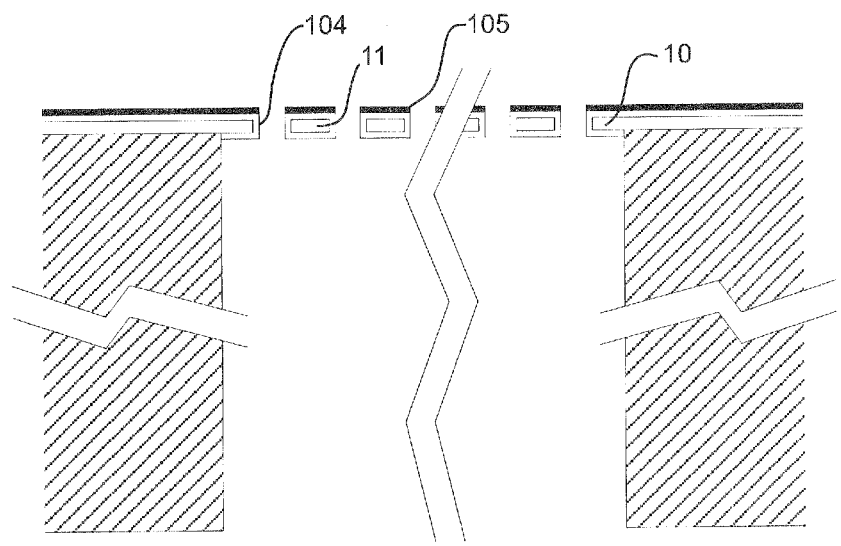
FIG. 11 is a cross section of a nozzle device with a coated nozzle plate.

Nozzle plates can be made substantially stronger (up to 250%) when the nearest distance 100 between all nozzle orifices and the nozzle plate support is at least six times the thickness of the nozzle plate FIG. 10A, 10B. The pressure strength of the nozzle plate may be further increased with at least 50% when the orifices are placed in a triangular or rectangular pattern 101 with respect to a long side of the nozzle plate support. Preferential the orifices are slit shaped and placed parallel along the width of the nozzle plate support, FIG. 10B. An organic coating 104, in particular a parylene coating on the nozzle plate may further increase the pressure strength of the nozzle plate. Also a bacteria killing surface modification 105 may be applied, for example a silver coating, FIG. 11. A silicon nitride coating on the nozzle plate and the nozzle plate support may also be provided to make the whole structure inert for acid and caustic.

Figure 12:
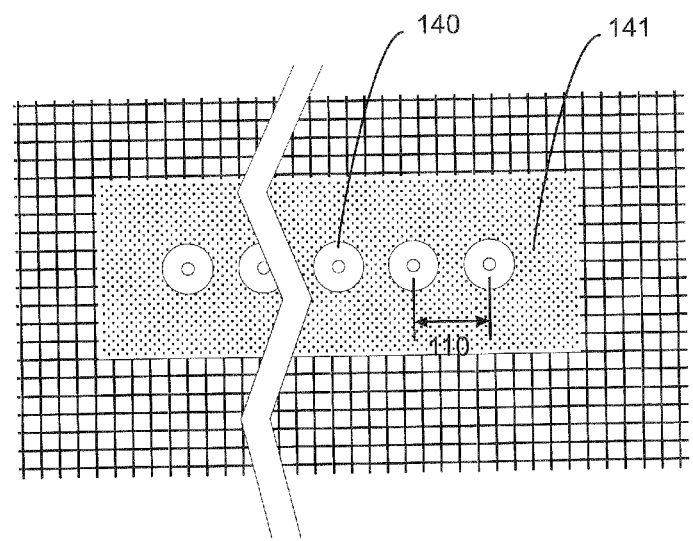
FIG. 12 is a top view of a nozzle plate with separated hydrophilic/hydrophobic membrane coating for improved jetting/jet start.
Figure 13:
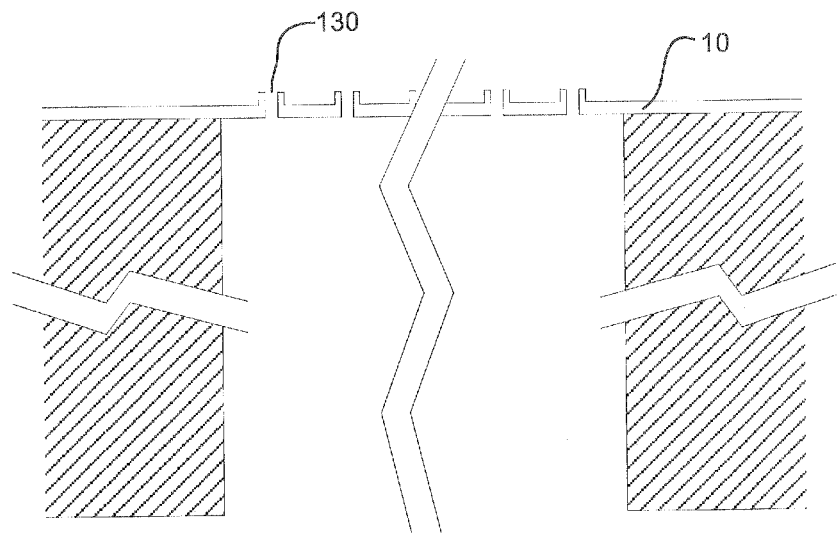
FIG. 13 is a cross section of a nozzle plate with slightly protruding nozzles.
Figure 14:
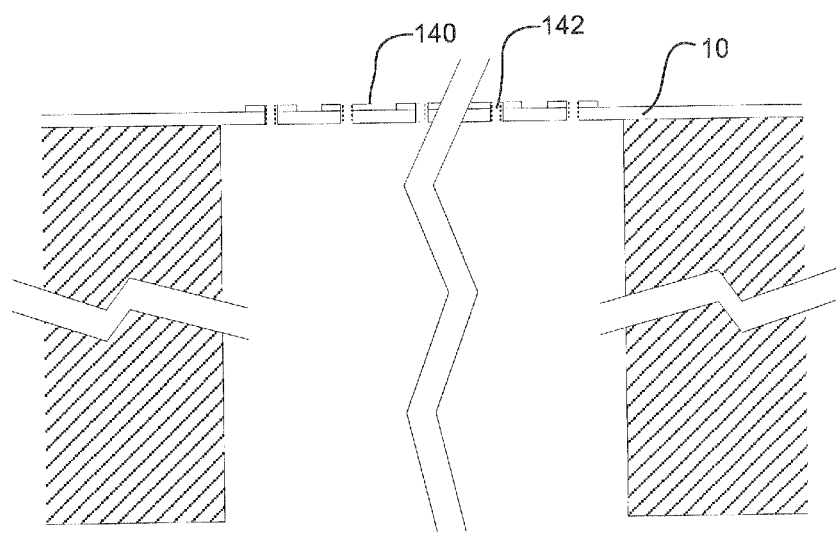
FIG. 14 is a cross section of a nozzle plate with hydrophilic/hydrophobic coatings around the orifices.
Figure 15:
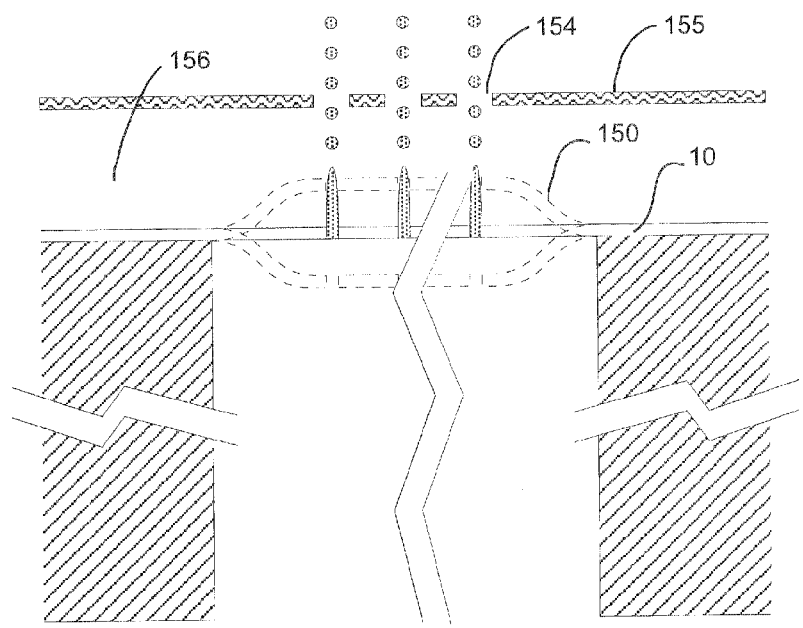
FIG. 15 is a cross section of a vibrating nozzle plate with drain plate.
Figure 16:
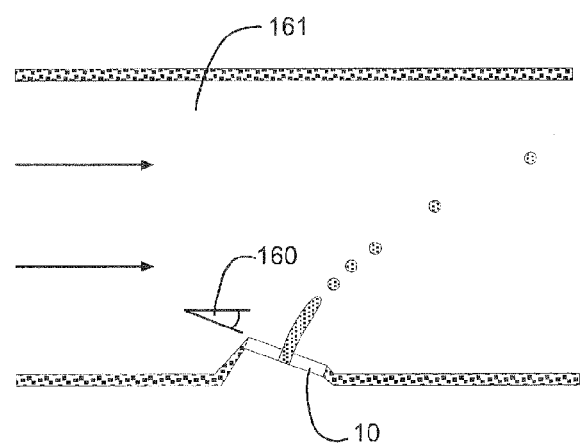
FIG. 16 is a cross section of nozzle plate, placed under an angle, in a cross flow channel.
Figure 17:
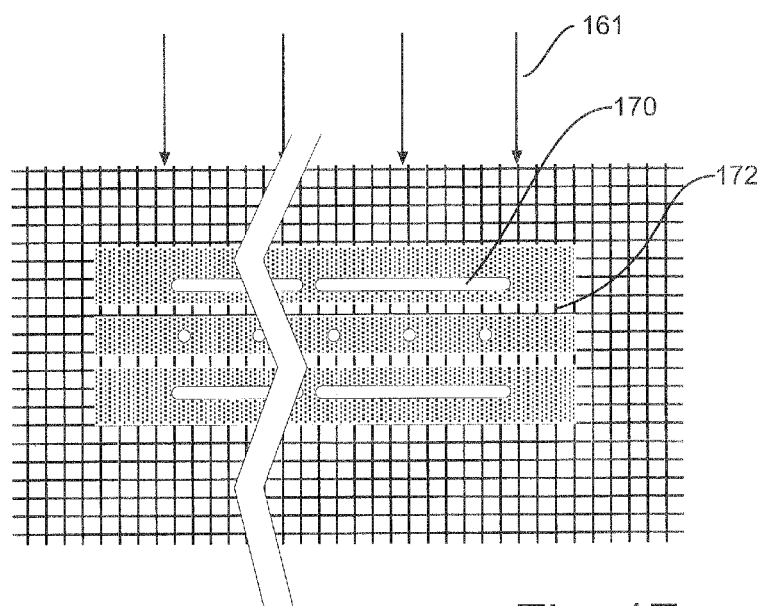
FIG. 17 is a top view of a nozzle plate with extra nozzles for co-flow.
Figure 18:
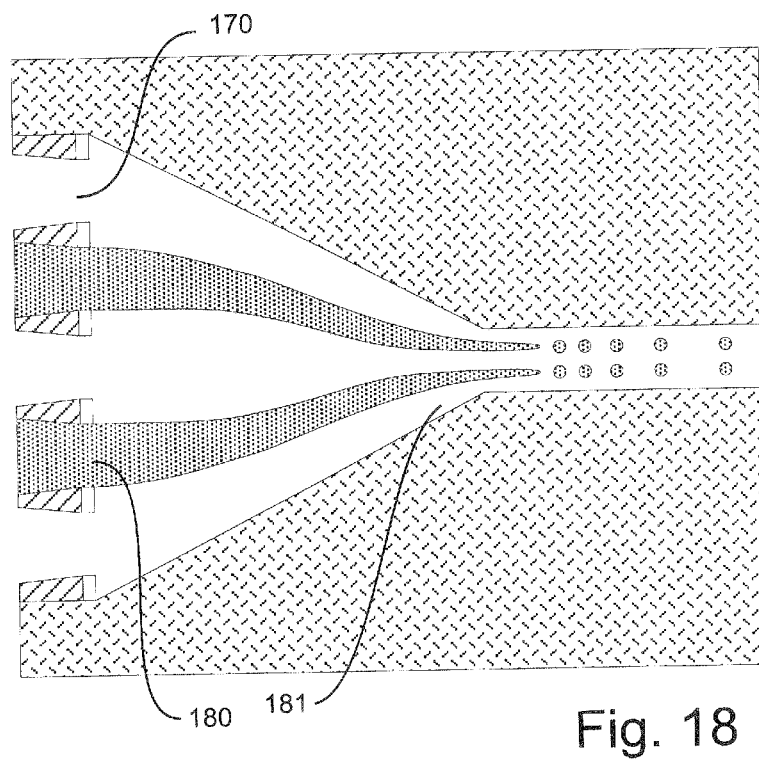
FIG. 18 is a cross section of a nozzle plate for emulsification.
Figure 19:
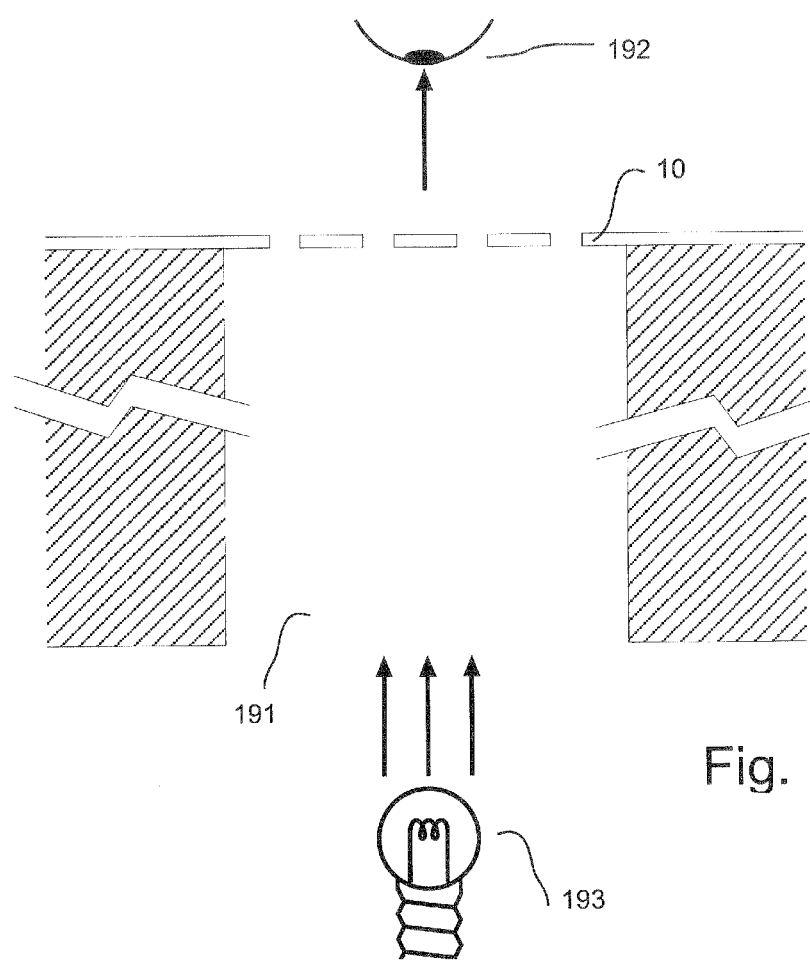
Figure 20:
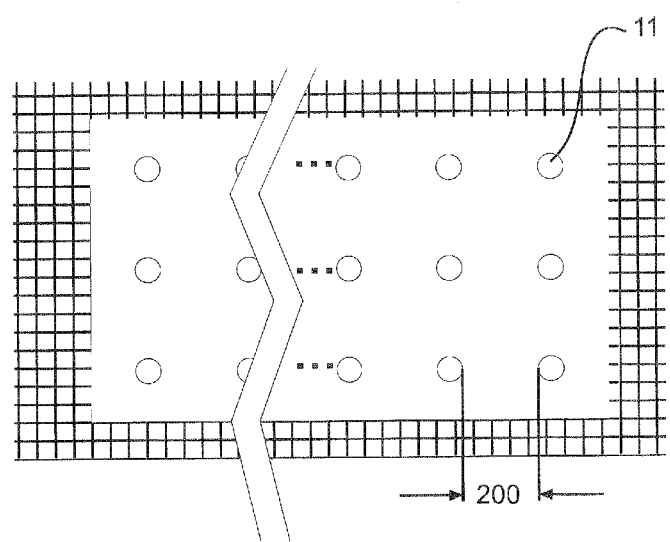
FIG. 20 is a top view of a filter for analysing particles that isolates the particles for enhanced recognition.
Figure 21:
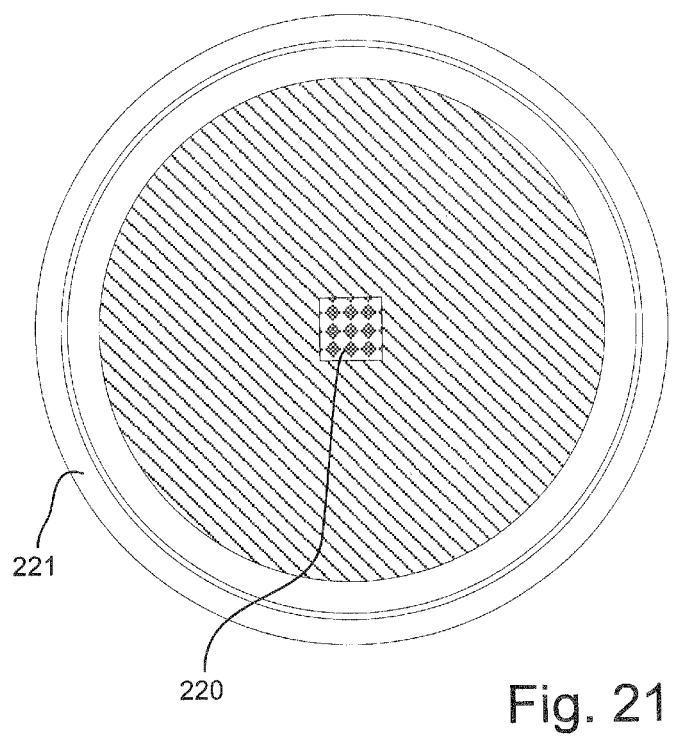
FIG. 21 is a top view of a plastic disc supporting a nozzle plate for analysis purposes.
Figure 22:
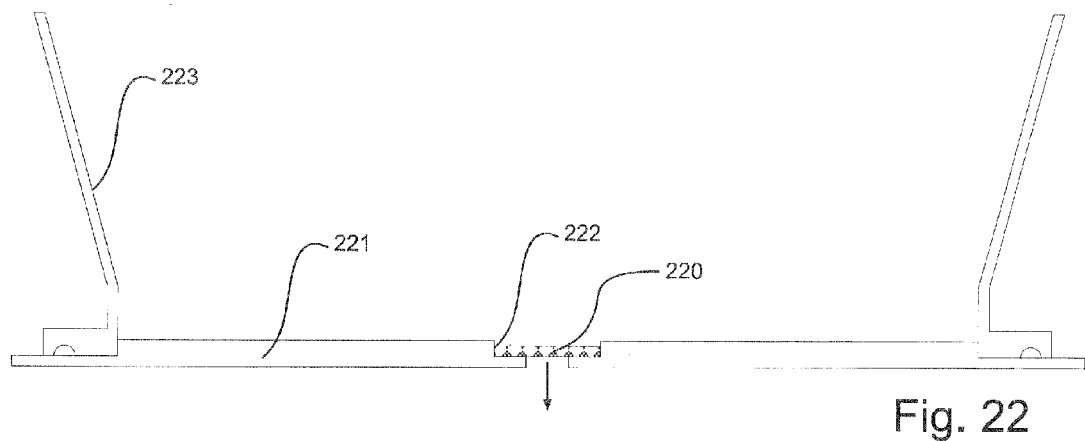
FIG. 22 is a cross section of a plastic disc supporting a nozzle plate for analysis purposes plus funnel.

A next embodiment of a nozzle for atomisation is shown in FIGS. 12, 13 and 14. The nozzle plate 10 with a thickness of 1 micron comprises circular orifices with a diameter of 0.8 micron. The distance between any of two orifices of the nozzle plate is larger than five times 110 the nozzle diameter in order to prevent recombination of droplets formed of nozzles next to each other. FIG. 13 shows a cross section of a nozzle plate wherein the orifices are slightly protruding out 130 of the surface (0.1-2 micron) of the nozzle plate 10. This measure is particular useful if the nozzle plate is used for jetting of a spray or emulsification because it prevents that the droplets will adhere to the surface of the nozzle plate just next to the nozzle orifice, resulting in to large droplet formation. In case of atomisation (FIG. 14) it is particular useful to make a small area (e.g. 2-5 micron radius around the nozzle) hydrophobic 140 to prevent droplet attachment/smearing and an unwanted increase of the jet diameter (confinement of the jet). Preferential the next surrounding area 141 should be made hydrophilic in order to drain a too large formed droplet that might inhibit jetting behaviour along the hydrophilic coated part of the nozzle plate. Good results have been obtained with a micro porous hydrophilic coating (PolyVinylPyrolidone/PolyEtherSulphone) with a thickness of a few micron on area 141. Alternatively capillary forces may be used to drain the droplet through e.g. the provision of a drain channel 156 with a height of e.g. 2 to 50 micron between the nozzle plate and an e.g. parallel placed drain plate 155 with an orifice 154 larger (e.g. 5 micron) than the jetting orifice (e.g. 1 micron), see FIG. 15. The jet will normally first pass the jetting orifice and next the larger orifice without fluid contact with the drain plate, but as soon as a droplet is formed that touches the drain plate it will be drained through the drain channel. A hydrophilic inner surface 142 of the nozzles of the nozzle plate is a good measure in order to suppress a large Pascal Pressure with at least 50%.

Jetting may be enhanced by using a piezoelectric actuator at a frequency between 100 kHz and 3 Mhz. Jetting may also be enhanced using the eigenresonance frequencies of the nozzle plate. This frequency should match the value of the initial jet velocity divided by two to two hundred times the diameter of the nozzle, typically a value between 50 kHz en 5 MHz. The eigenresonance frequency is mainly determined by the mass and a fortiori lateral dimensions of the free hanging nozzle plate (typical 1×10×10 micron to 4×250×2000 micron), the rigidity of and the tensile pre-stress in the nozzle plate (typical $10^6$to $10^9$ Pascal). A vibrating nozzle plate 150 is shown in FIG. 15 Measures to prevent droplet coalescence include: to charge the droplets during droplet formation with an external voltage, or by friction (tribocharging) of the fluid in the nozzle plate device, or by friction of the droplets with the air. An electrical connection (short-circuit) between the patient and the atomising device may be necessary (patient serves as an earth electrode). Further measures include placing the nozzle plate at an angle 160 between 10 and 90 in a cross flow channel 161, particularly useful for Rayleigh break-up (FIG. 16) or co-flow of air or another medium through separate nozzles orifices. Good results have been obtained with a nozzle plate design (FIG. 17) in which the nozzles for atomisation are lined up and the nozzles for co-flow 170 are lined up perpendicular to the cross flow channel. The nozzles for the liquid and the nozzles for the air have separated 172 supply channels. For emulsification it is particularly useful to place the nozzle plate in a dead-end configuration in the channel, which channel 181 narrows significantly at the downstream side. With relatively large nozzle orifices it is then possible to make very small emulsion droplets or gasbubbles (FIG. 18) at least 2-10 times smaller than the diameter of the smallest nozzles 180. Double emulsions (o/w/o or w/o/w) can advantageously be made with this device, because small emulsion droplets can easily pass the larger orifices without coalescense.

FIGS. 19 and 20 show an embodiment of a filter means or nozzle for retaining particles. The nozzle plate support body is made out of one silicon <110> wafer. With this type of crystal orientation it is possible to make perpendicular openings in the support by use of wet (KOH) etching. When the width between two walls of the nozzle plate support body 191 is chosen small (e.g. 20 micron) it is possible to make a high flow resistance in the nozzle cavity. For filtration purposes it has proven to be useful to make an open porosity higher than 30%, not only because of the high flux, but also because it is then relatively easy to back-flush the membrane to prevent irreversible fouling.

The nozzle plate may also be used for retaining and subsequent microscopic observation 192 of these particles, e.g. bacteria's, yeast cell's, blood cell's, etc. Fluorescent dyes may be used to simplify and identify specific species of the micro-organisms on the filter. Silicon nitride and other inorganic nozzle plate materials have the advantage in contrast to many organic polymeric materials that there is virtually no auto-fluorescence signal from the material itself. In some cases it is convenient to place the nozzle orifices further apart, in order to isolate the micro-organisms from each other for a more easy recognition and enumeration.

Very useful nozzle plates for this purpose are characterised in that the spacing 200 between the nozzle orifices is minimum three and maximum thirty times the diameter of the nozzle orifices.

Filter means or nozzles may be used for disposable filtration applications, with preference small nozzle plates 220 (e.g. 5×5 mm) are embedded in a ring shaped support 221 (e.g. ABS plastic discs) with outer dimension of e.g. 1.0, 2.5 and 5 cm in diameter and ready to use in standardised commercial filtration holders. With preference the nozzle plates are countersink 222 with a depth of 10 to 500 micron in the ring shaped support to prevent contamination, to facilitate packaging and mechanical rupture of the nozzle plate (FIG. 22).

Figure 23:
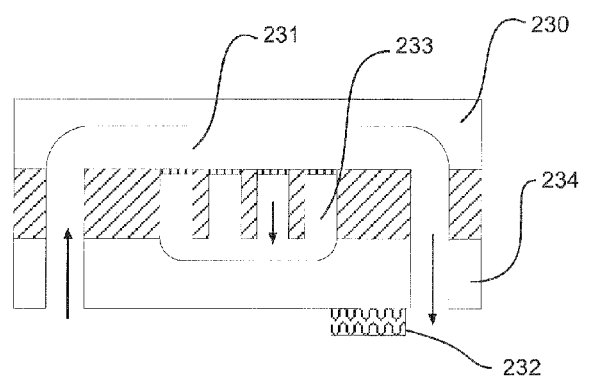
FIG. 23 is a cross section of a reusable nozzle plate with a transparent cross flow channel.

For reusable application an optic transparent cover slip 230 is placed over the nozzle plate in such a way that a cross-flow channel 231 with a depth of 50 to 500 micron exists between the nozzle plate and the cover plate (FIG. 23). With preference the cover plate is a glass like material that is anodically bonded to the nozzle plate or the nozzle plate support body at elevated temperature (300-400 C) at a voltage between 500 and 1500 V. Cleaning and reuse of this device is facilitated 232 by using ultrasound with a frequency between 100 kHz and 1 MHz. A liquid handling board 234 can be made in glass (with a preferred thickness between 0.5 and 11 mm) for supply of liquid to and from the nozzle plate. By using an anodic bond between the nozzle plate or the nozzle plate support body and the liquid handling board, glass can be used as a liquid handling board for applications in which the required pressures are higher than 0.8 bar.

Figure 28:
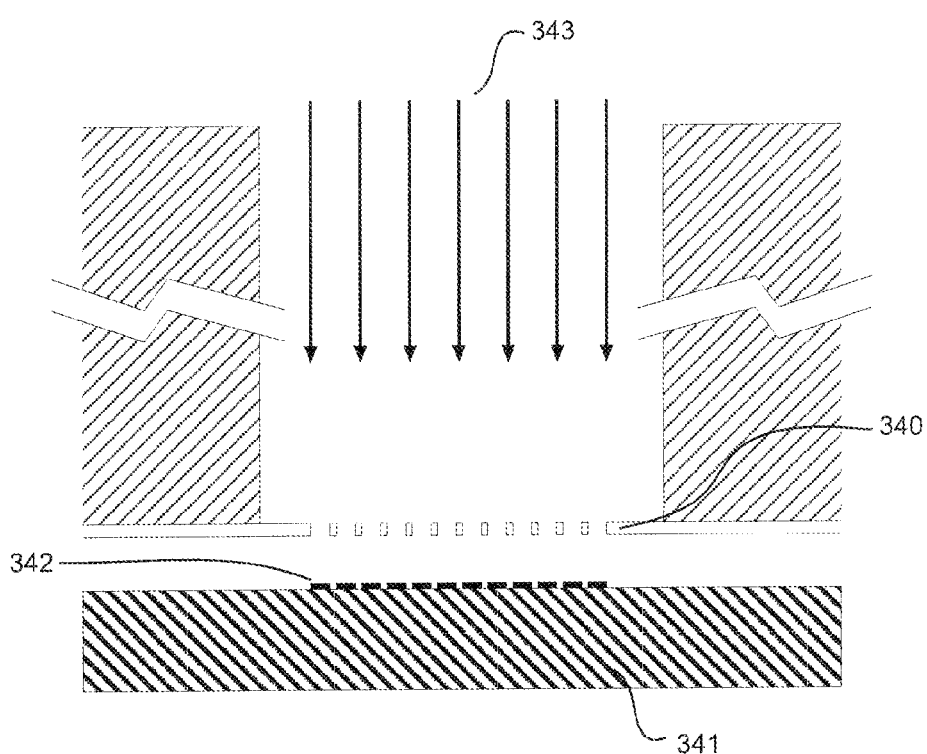
FIG. 28 is cross section of a nozzle plate for evaporation purposes.

With preference the nozzle plate support body has cavities 233 with at least the same size as the nozzle plate. It is then possible to use a microscope 192 with a light source that projects light 193 first through the nozzle support and next on the nozzle plate. Most microscopes with phase contrast mode work in this manner. FIG. 28 shows a nozzle plate 340 that can also be used for the deposition (stencilling) 343 of isolated material spots 342 on a substrate 341 with feature sizes determined by the lay out of the nozzle plate. <110> silicon is a good support material for the nozzle plate for these purposes.

Large nozzle plates with an outer circular diameter of e.g. 2, 3, 4, 6 and 8 inches may be used for micro filtration applications like yeast cell filtration and clarification of beer and other beverages. Sterile filtration of milk and other dairy products is also possible with pore sizes between 5 and 0.22 micron. With a pore size of 0.8 micron it has been tested that a log reduction of 5 to 6 of micro-organisms in milk is well achievable in combination with back-pulse (pulsed permeate flow reversal) technology. Typical flow rates are 1000-2000 l/m$^2$/hour at low trans-membrane pressures (0.03-0.1 bar) with a back-pulse rate of 0.01-5 Hz. The flow rate can be strongly increased (4000-20.000 l/m$^2$/hour) using ultrasound in a broad frequency spectrum between 100 Hz-1 MHz. Preferably a frequency is used under 15 kHz or above 50 kHz in order to suppress the cavitation forces that might disrupt the nozzle plates between 15 kHz and 50 kHz. The ultrasound inhibits the forming of a dense cake layer just before the nozzle plate. Alternatively the performance for jetting, filtering, foaming and emulsification may be improved by moving the nozzle plate tangential and/or orthogonal to the fluid in contact with the nozzle plate with an actuator with an amplitude of 0.1 to 100 micron and a frequency of 10 Hz-10 MHz.

Figure 24:
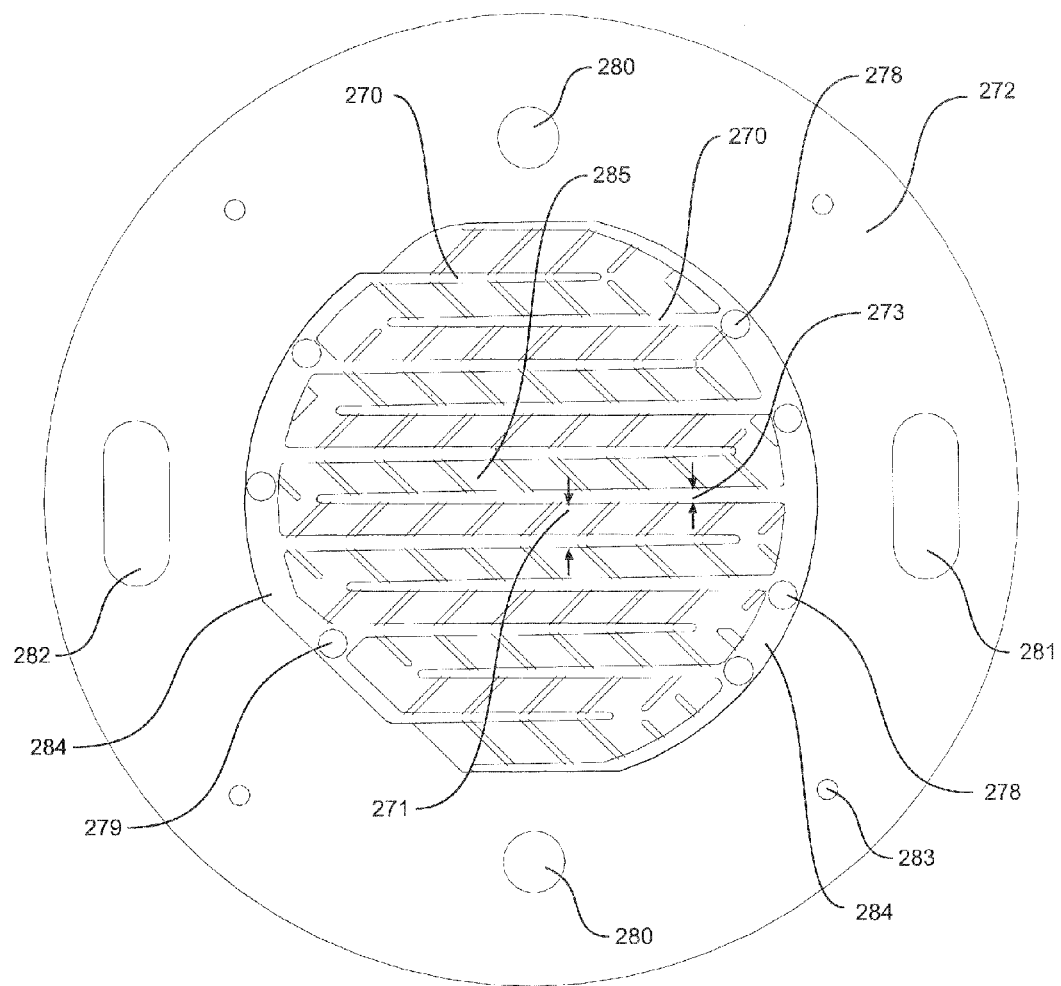
FIG. 24 is a top view of a glass module plate for high volume nozzle plates.
Figure 25:
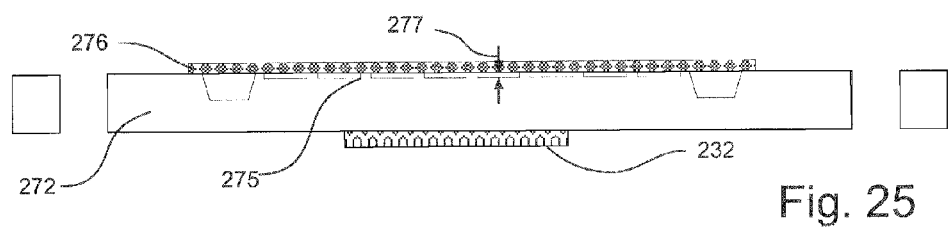
FIG. 25 is a cross section of a glass module plate for high volume nozzle plates showing the shallow cross flow channels.
Figure 26:
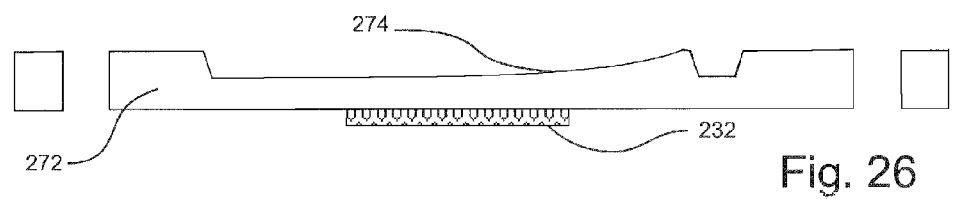
FIG. 26 is a cross section of a glass module plate for high volume nozzle plates showing a channel of the comb structure.
Figure 27A:
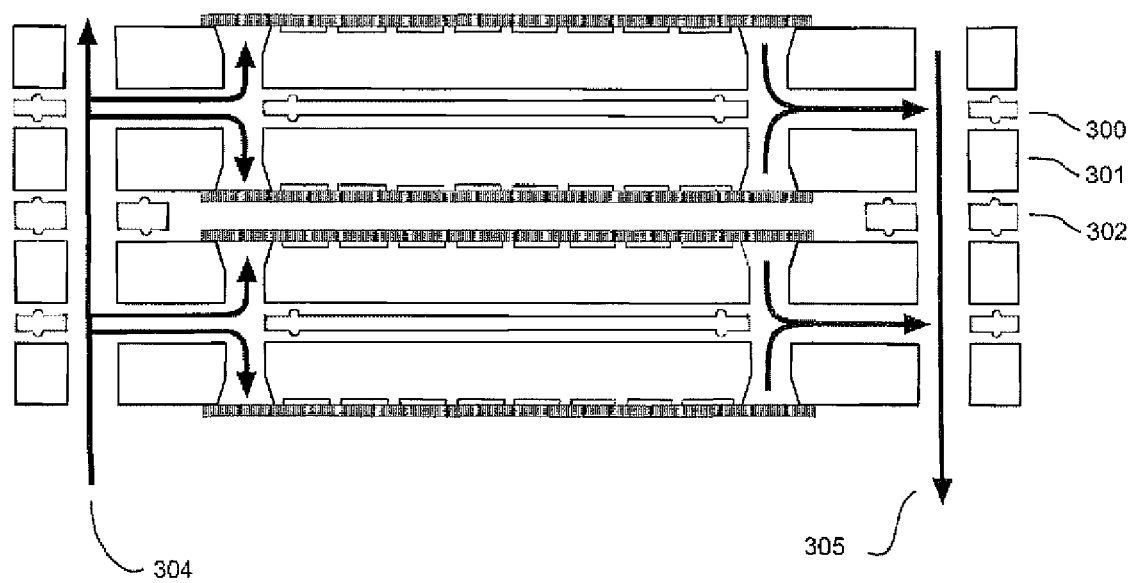
FIG. 27A is a cross section of stacked module plates.
Figure 27B:
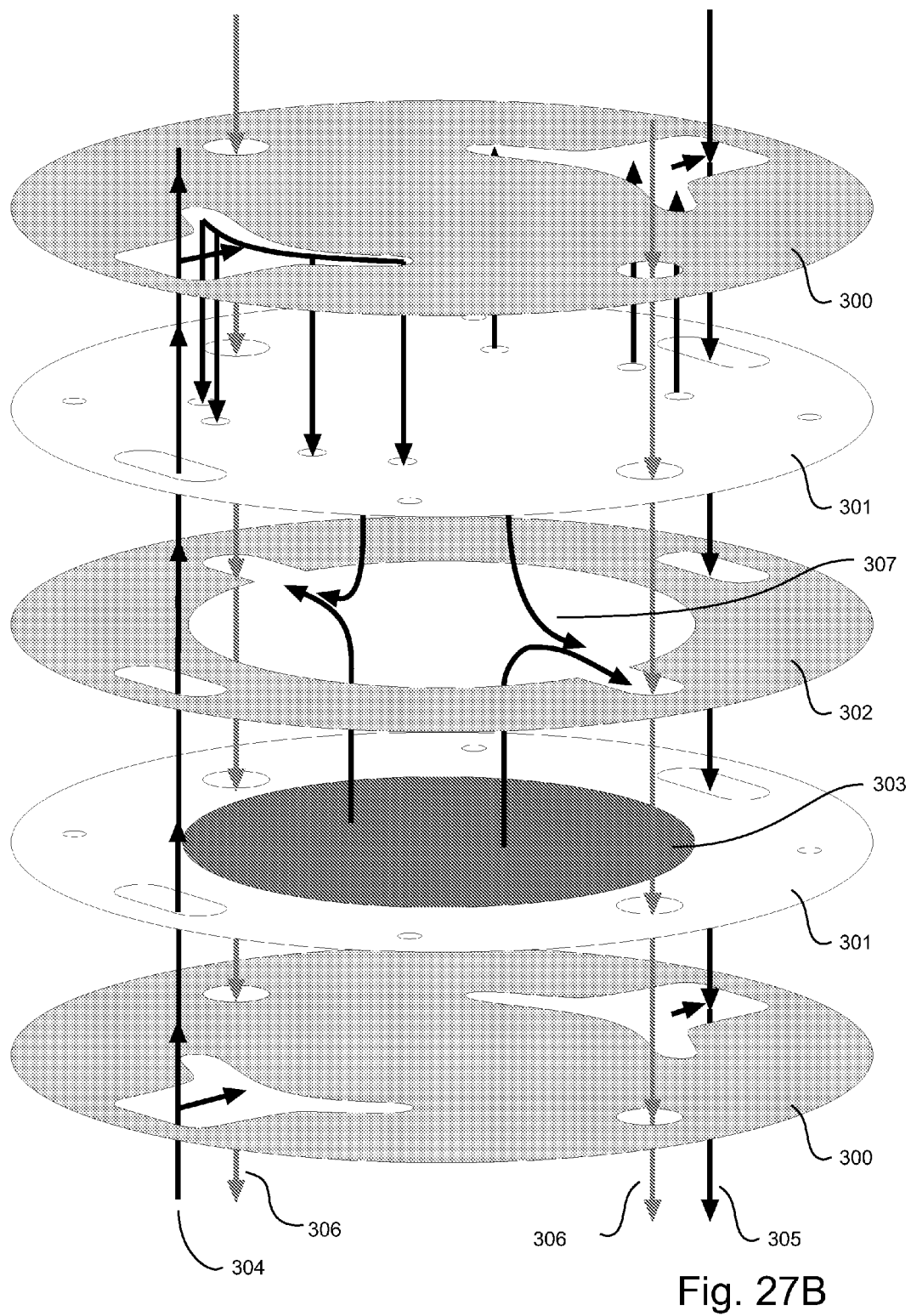
FIG. 27B is a opened 3D view of stacked module plates showing the liquid flow within the stack.

In a special embodiment the nozzle plates or nozzle plate support bodies are bonded to a glass plate in which flow channels 270, 284 have been made with the use of grinding or powder blasting (FIGS. 24, 25 and 26). Glass plates of type borosilicate have the advantage that they are very flat, have nearly the same thermal expansion coefficient $4.10^{-6}$° C. as nozzle plates with a silicon support. Anodic bonding results in a bond inert for acid, caustic and oxydizing chemicals. The flow channels may be used for permeate flow or alternatively for cross-flow. Preferably the flow channels for cross-flow are placed in comb like structures which taper in length and/or in height. The comb structure has the advantage that the total pressure drop over the shallow channel area 285, the comb teethes 270, the inlet 278 and outlet 279 (through the glass plate) can be kept low (less than 100 mBar), while the cross flow speed at the nozzle plate surface (at the shallow channel area 285) is yet high enough (more than 0.1 m/s) for the enhancement of continuous removal of particles and yeast cells during filtration. The distance 271 between the teethes 270 of each comb are preferably 0.5-5 cm, with a depth of 1-5 mm, a width of 1-5 mm and a length depending on the outer circular diameter. The tapering of the depth 274 is preferably 10° to 40°. The width 273 is preferably tapering 10-40% per cm length of the channel. In particular when powder blasting is used to manufacture the channels in the glass plate, there is a triangular shape of the channels with a relation of the width of the channel and the depth if 1.2. The tapering is meant for a good redistribution of the fluid from the incoming channel to the outgoing channel in such a way that the pressure distribution along a single tooth of the cross flow channels is homogeneous while the fluid velocity never reaches zero to avoid hygienic failure. The pressure drop over every single tooth is equal by varying the width and the depth of the tooth. The mean cross flow height between the glass plate and the nozzle plate 276 in the shallow channel area is preferably between 0.1 and 1 mm. As well the cross-flow side as the permeate side may be bonded to a glass plate, also one glass plate may be bonded on both sides with a nozzle plate device. With preference the glass plate is being used for a filtration module, where a larger filtration capacity is achieved by placing a number of nozzle plate devices 301 with spacer structures 300, 302 in a stack (plate and frame module with mirror placing of the glass plate 301 and the nozzle plates 303, FIG. 27A, 27B. The glass plate acts in this module also as tubing for the cross flow inlet 281, 304, cross flow outlet 282, 305 and permeate collection 280, 306, 307. Furthermore, the glass plate may contain holes 283 for easy positioning of the glass plate and the spacer structures. Filtration characteristics may also be enhanced by using rotating nozzle plates with respect to the medium in a module. A piezo transducer for ultrasound can be placed on the back side (non powder blasted side) of each glass plate. A typical longitudinal resonance frequency of a glass plate with a thickness of 10 mm is 250 kHz. The ultrasound may be used either for enhancement of the flow rate during filtration or for cleaning of the nozzle plates after or during the filtration cycle. Of course cleaning after filtration with ultrasound is accelerated using proper chemicals (acid/caustic/enzymes etc.). Normal chemical cleaning procedures as used for micro and ultra filtration membranes can herewith be reduced from 1-2 hours back to 10 seconds-5 minutes. Cross-flow cleaning on both sides of the nozzle plate is enhanced by the interconnection in one or more directions of all nozzle support openings.

Nozzle plates made with a silicon support can be made chemically inert for caustic media by providing a thin LPCVD grown silicon nitride coating with a typical thickness between 0.01 and 1 micron. Other organic and inorganic coatings like e.g. $Al_2O_3$, $TiO_2$, $ZrO2$, $ZrO2/Si_3N_4$ may be applied to alter the Zeta potential and/or the wetting properties of the nozzle plate to improve filtration characteristics. Other coatings may also be applied to promote anti-fouling like $TiO_2$, PTFE, self assembling monolayers (SAM, e.g. based on nitryls, disulfides or thiols) or long polymer chains (e.g. polyethyleneglycol) coupled with an end- or side-group to the nozzleplate. Dense sol/gel coatings or gas permeation layers like Pd, PdAg may also be applied over and in the nozzle orifices to make ultrafiltration and gas filtration membranes.

An important insight according to the invention is that the combination of nozzle plates, back-pulse technology and ultrasound has proven to be very powerful for the enhancement of flow rate and the prevention of irreversible fouling. Without ultrasound a typical clarification run for beer is 4-8 hours, with ultrasound dosed at intervals of 10 minutes for a few seconds the run can be extended to 4-8 days without the need of chemical cleaning procedures.

Backpulsing for a very short time 10-50 ms at regular intervals 0.01-5 Hz during cross-flow filtration at low transmembrane pressure will lift the cake layer from the nozzle plate and will inject it higher in the cross flow channel where the fluid velocity is sufficient high to take it further away.

Backpulsers are also very suitable to use for up-concentration of samples for the detection and counting of food spoiling or pathogenic micro-organisms, e.g. lacto bacillus, *E-coli* and *legionella*. After the up-concentration all micro-organisms are present on the nozzle plate and can be processed for e.g. microscopic observation and PCR amplification. Small nozzle plates of e.g. 4×4 mm can be put easily with a clean and sterile pincer in a small PCR-cup. The nozzle plate can also be provided with an immuno binding (or elisa coupling) agent for the selective binding of certain species direct to the nozzle plate during filtration, especially when cross-flow techniques are used for up-concentration of the sample. Magnetic layers may also be deposited for the attraction of immuno magnetic beads. Metallic layers may also be provided on the nozzle plates for e.g. optic non-transparancy, non quenching or electrolysis applications, improvement of filtration under the applicance of a small voltage difference between the fluid and the nozzle plate, or the annihilation(electroporation) of microorganisms under the applicance of a high voltage pulse. Platina may be deposited in electrical resistor strips on the nozzle plate for heating purposes. Also a bacteria killing surface modification may be applied, for example a silver coating. Piezo materials may also be applied for direct vibration of the nozzle plates or for the detection of bending of the nozzle plates for pressure registration. The intensity and the frequency of the backpulsers may also be regulated by the registration of the nozzle plate trans membrane pressure. The trans membrane pressure will normally increase if there is a built up of a cake layer for the nozzle plate.

Nozzle plates can be made in various ways according to the invention.

A reinforced micromachined polymeric nozzle plate is made by
    depositing a first layer of a photosensitive material, for example negative resist polyimide (Durimide 7510) on a flat and smooth substrate
    exposing the first layer to a suitable light source through a mask (or a laser interference pattern) with a nozzle pattern
    developing and if necessary curing the first layer
    depositing a second layer of a photosensitive material onto the first layer
    exposing the second layer to a suitable light source through a mask with a nozzle support structure
    developing and if necessary curing the second layer
    releasing the thus obtained nozzle plate from the substrate
Another method of making a micromachined polymeric nozzle plate, comprises the following steps
    depositing a first layer of a photosensitive material on a flat and smooth substrate
    exposing the first layer to a suitable light source through a mask (or laser interference) with a nozzle pattern
    developing the first layer
    etching anisotropically the nozzle pattern to a certain depth, typically 1 to 5 micron, in the substrate
    depositing a second layer of a photosensitive material onto the substrate
    exposing the second layer to a suitable light source through a mask with a nozzle support structure
    developing the second layer
    etching anisotropically the nozzle support structure to a certain depth, typically 5 to 500 micron, in the substrate
    electroforming a master mould from the substrate if necessary or using the substrate itself as a master mould
    if necessary depositing a release agent (teflon) on the master mould
    placing a thin sheet of thermoplastic polymer with a typical thickness between 5 and 50 micron onto the master mould
    placing a second (flat) substrate with a release agent on the polymeric sheet
    pressing the two substrates to each other with a substantial load at a temperature well above the glass transition temperature of the polymeric sheet if necessary under reduced atmospheric conditions for a short period
    releasing the thus formed polymeric nozzle plate from the substrates at a temperature well below the glass transition temperature
A reinforced micromachined electroformed nozzle plate is made by
    depositing a conductive layer on a flat and smooth electrically insulating substrate
    depositing a first layer of a photosensitive material on the conductive layer
    exposing the first layer to a suitable light source through a mask with a nozzle support pattern
    developing the first layer
    etching the conductive layer with a suitable chemical etchant
    removing the first layer
    depositing a second layer of a photosensitive material with a thickness of at least 2 micron onto the substrate
    exposing the second layer to a suitable light source through a mask with a nozzle device
    developing the second layer such that the remaining resist layer is not in contact with the conductive layer
    putting the substrate in a suitable electroforming bath using the conductive layer as a cathode
    stopping the electroforming process as soon as the electroformed layer has reached substantially at least one or more parts of the remaining resist layer
    releasing the thus electroformed nozzleplate
Another method of making a micromachined nozzle plate device comprises the following steps
    depositing a first layer of a photosensitive material on a flat and smooth substrate, said substrate being covered at both sides with a thin membrane layer
    exposing the first layer to a suitable light source through a mask with a nozzle support pattern
    developing the first layer
    etching the nozzle support pattern in the membrane layer on one side of the substrate and further
    etching chemically the nozzle support pattern through the substrate stopping at a distance of 5 to 100 micron of the membrane layer at the other side of the substrate
    depositing a second layer of a photosensitive material onto the other membrane layer of the substrate exposing the second layer to a suitable light source through a mask (or laserinterference) with a nozzle plate structure developing the second layer etching the nozzle plate structure in the membrane layer etching through the nozzles part of the nozzle support structure such that the nearest distance between the nozzles and the nozzle support structure is at least twice the nozzle diameter Nozzle plates according to the invention may also be used for the extrusion of very viscous media like macromolecular solutions, gel-like solutions and protein-rich media, and for microstructuring of food and pharmaceutical products like e.g. synthetic meat (fibres).

Nozzle plates according to the invention may also used for micro-array and micro-titration applications, to make double emulsions and to apply them in bio-capsules because of the small diffusion length of the short nozzle orifice.

The invention claimed is:

1. A fluid filtration device, comprising:
a support body having a first main surface side and having a functional plate at said first main surface side, the functional plate having a thickness of less than 2 microns and comprising a plurality of orifices penetrating through said thickness of said functional plate,
wherein the support body forms a cavity underneath said functional plate and said plurality of orifices,
wherein an orifice within said plurality of orifices has a length less than six times a diameter of said orifice,
wherein said plurality of orifices are arranged closely together in a group of orifices in a first zone of said functional plate,
wherein said functional plate comprises a second zone along a boundary of the cavity, said second zone surrounding said first zone and said second zone being substantially free of any orifice,
wherein said second zone extends over a width between said boundary and across from said first zone which is at least a plurality of times as large as said thickness of said functional plate, and
wherein, at said main surface, said cavity has a cross-section with a width of less than 250 microns.

2. A filtration device for filtration of a fluid, comprising:
a support body having a first main surface side and carrying a functional plate at said first main surface side of said support body, the functional plate having a thickness of less than 2 microns and comprising a plurality of orifices extending over said thickness through said functional plate,
wherein the support body has a cavity underneath said functional plate and said plurality of orifices,
wherein an orifice within said plurality of orifices has a length less than six times a diameter of said orifice,
wherein said plurality of orifices are arranged in a first zone of said functional plate,
wherein said functional plate comprises a second zone adjacent said first zone which is substantially free of any orifice,
wherein said cavity extends to both said first zone and said second zone of said functional plate,
wherein said second zone extends over a width across from said first zone which is at least a multiple of said thickness of said functional plate, and
wherein, at said main surface, said cavity has a cross-section with a width of less than 250 microns.

3. The filtration device according to claim 2, wherein said at least one orifice in said functional plate has a diameter between 0.4 and 10 microns.

4. The filtration device according to claim 2, wherein said cross-section has a length of more than 300 microns.

5. The filtration device according to claim 2,
wherein said support body comprises a silicon substrate, and
wherein said functional plate comprises a separate layer provided on said substrate.

6. The filtration device according to claim 5, wherein said functional plate comprises a rigid, chemically inert layer with a high fracture stress.

7. The filtration device according to claim 6, wherein the chemically inert layer is silicon nitride.

8. The filtration device according to claim 5, wherein said silicon substrate is formed from a silicon wafer.

9. The filtration device according to claim 8, wherein said silicon wafer is a <110>silicon wafer.

10. The filtration device according to claim 2, wherein said support body is suspended in a ring shaped support frame adapted to respective dimensions of a commercially available filter holder.

11. The filtration device according to claim 10, wherein said functional plate is countersunk to a depth of between 10 and 500 microns in the ring shaped support frame.

12. The filtration device according to claim 2, wherein said cavity exposes at least substantially an entire active portion of said functional plate for enabling full microscopic observation.

13. The filtration device according to claim 2, wherein the length of said orifice is shorter than the diameter of said orifice.

* * * * *